United States Patent
Ashby et al.

[11] Patent Number: 5,609,644
[45] Date of Patent: Mar. 11, 1997

[54] PROSTHETIC PATELLO FEMORAL JOINT ASSEMBLY

[75] Inventors: Alan M. Ashby, Caen, France; Lindsay Laird, New Lambton Heights, Australia

[73] Assignee: Howmedica International, Shannon, Ireland

[21] Appl. No.: 409,116

[22] Filed: Mar. 22, 1995

[30] Foreign Application Priority Data

Mar. 23, 1994 [GB] United Kingdom ............... 9405746

[51] Int. Cl.$^6$ .................................................. A61F 2/38
[52] U.S. Cl. ............................................. 623/20; 623/18
[58] Field of Search ............................ 623/20, 18, 16

[56] References Cited

U.S. PATENT DOCUMENTS

| | | |
|---|---|---|
| 4,007,495 | 2/1977 | Frazier . |
| 4,041,550 | 8/1977 | Frazier . |
| 4,085,466 | 4/1978 | Goodfellow ........................... 623/20 |
| 4,151,615 | 5/1979 | Hall . |
| 4,309,778 | 1/1982 | Buechel ................................ 623/20 |
| 5,246,460 | 9/1993 | Goodfellow ........................... 623/20 |
| 5,314,480 | 5/1994 | Elloy et al. ........................... 623/20 |

FOREIGN PATENT DOCUMENTS

| | | |
|---|---|---|
| 0038896A1 | 11/1981 | European Pat. Off. . |
| 0497955B1 | 9/1994 | European Pat. Off. . |
| 2663839 | 1/1992 | France . |
| 2700260 | 7/1994 | France ................................ 623/20 |
| 2247407 | 1/1994 | United Kingdom . |
| 2277034 | 10/1994 | United Kingdom . |
| WOA9203109 | 3/1992 | WIPO . |

*Primary Examiner*—David H. Willse
*Assistant Examiner*—Bruce E. Snow
*Attorney, Agent, or Firm*—Peter C. Richardson; Lawrence C. Akers; Raymond W. Augustin

[57] ABSTRACT

A prosthetic patello femoral joint assembly comprises a patella mounting component on which is located a movable mobile bearing component. A first side of the bearing component is shaped to engage the patella groove of a natural or an artificial femur. A second side of the mounting component has a substantially spherical convex bearing surface which engages and can articulate against a substantially spherical posterior concave bearing surface on the mounting component. A control means acts between the components to restrict substantially vertical movement of the bearing component about a medio lateral axis of the knee with which it is to be used, but allows substantially horizontal movement and relative rotation between said mounting component and said bearing component.

5 Claims, 4 Drawing Sheets

PROSTHETIC PATELLO FEMORAL JOINT ASSEMBLY

BACKGROUND OF THE INVENTION

1. Field of the Invention

This invention relates to a prosthetic patello femoral joint assembly.

2. Description of the Prior Art

The patello femoral joint experiences very large contact forces in balancing the flexion moment across the knee. In ascending and descending stairs, the contact force on the patello femoral joint has been biomechanically calculated as lying in the region up to six times body weight.

Previous designs of patello femoral articulation have compromised between the contact conformity of the patella articulating surface against the femur and the need to accommodate variations introduced by surgical inaccuracy, patient anatomical variation and the movement required from the articulation without inducing averse fixation forces or inappropriate contact conditions.

In general, due to the lack of precise datums, it is very difficult surgically to arrange for the rotational positioning of the patella component so that it precisely matches the orientation of the patello femoral groove geometry on the femoral implant component. The majority of designs in the market place therefore use an axisymmetric configuration for the bearing surface of the patella component. This inevitably results in low conformity between this part and the femur. The maximum conformity possible being a line contact. This results in high stresses in the plastic articulating material of the patella component with premature wear. Alternative designs with saddle shaped articulations on the patella component have been prone to a different type of problem. These components theoretically allow for a larger contact surface between the patella component and the femur, but are extremely sensitive to alignment. When surgical accuracy is not absolute, the error in alignment causes edge loading, and excessive fixation loading of the patella component.

Designs of patella resurfacing components which incorporate a trunnion to allow the appropriate rotational orientation of a more conforming patella bearing surface have been proposed. These include the designs of Buechal and Papas (U.S. Pat. No. 4,309,778). Nevertheless, these devices still have a high dependence on surgical accuracy to ensure that the medio lateral positioning of the patella component, and the relative inclination of the component to the transverse plane of the patella bone, is appropriate. The currently proposed invention aims to overcome these problems.

SUMMARY OF THE INVENTION

According to the present invention a prosthetic patello femoral joint assembly comprises a patella mounting component on which is located a movable mobile bearing component, a first side of which is shaped to engage the patella groove of a natural or an artificial femur, and a second side of which has a substantially spherical concave bearing surface which engages and can articulate against a substantially spherical posterior convex bearing surface on said mounting component, and control means acting between the components which restrict substantially vertical movement of the bearing component about a medio lateral axis of the knee with which it is to be used, but allow substantially horizontal movement and relative rotation between said mounting component and said bearing component.

The patella mounting component may be fixed into the patella bone stock using any one of the already well known techniques including the uses of cement, pegs, expanding fins, ingrowth surfaces and any other suitable arrangement after the preparation of the appropriate fixation surface of in the bone. Preferably, said control means comprise a peg carried on said mounting component which engages a substantially horizontal slot in said bearing component. The peg may comprise a cylindrical or conical part with a capturing end feature or flange at its posterior end which is held in a re-entrant capture relationship in an undercut in said horizontal slot.

The mounting component may be manufactured from any one of the number of metallic, plastic or ceramic materials currently used for implant construction. The preferred material for this component in the present invention is a cobalt chrome molybdenum alloy.

The bearing component can be constructed from a resilient material, the conventional best choice for this material being ultra high molecular weight polyethylene. If the bearing component bears on the natural femur, then a ceramic or metal material from the range currently used for implant construction and may be used.

In a preferred construction, second control means are provided which act to limit relative rotational movement between said mounting component and said bearing component. This avoids the bearing component adopting an inappropriate orientation relative to the mounting component. These control means may comprise a pin which engages a second slot in said bearing component. Preferably the pin is a loose fit with a wide clearance in said second slot.

The second slot can be substantially parallel with said first slot and said pin can be a loose fit with a wide clearance in said second slot to allow limited rotation of said bearing component about said peg, said rotation being accommodated within the loose fit clearance of the pin in the second slot, regardless of the relative medio lateral position of the bearing and mounding components.

The invention also includes a prosthetic assembly as set forth above provided with a prosthetic femur component adapted for connection to a suitably prepared femur and which is provided with a patella groove to receive said bearing component.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
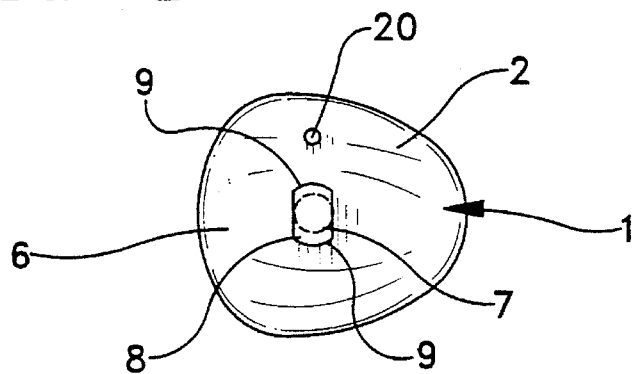
FIG. 1 is a posterior elevation of a patella mounting element for use in the invention.
Figure 2:
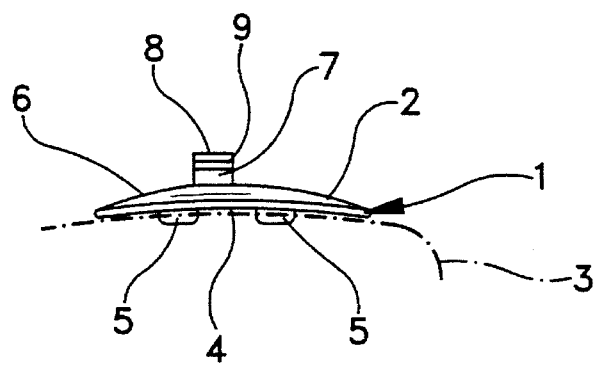
FIG. 2 is a plan view of the element shown in FIG. 1.
Figure 3:
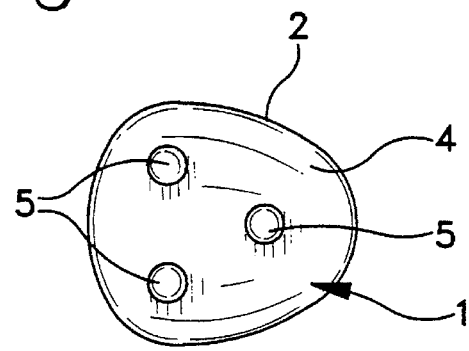
FIG. 3 is a front elevation of the element shown in FIG. 1.

FIGS. 1, 2 and 3 show a patella mounting element for use in the present invention. The element 1 is in the form of a convex dish 2 which is made from any suitable material but in the present embodiment is made from a cobalt chrome molybdenum alloy. The dish 2 is shaped to accept the remnant of a patella after fixation preparation indicated by broken lines 3 and is shaped appropriately. The front face 4 of the dish 2 is concave and carries three bosses 5 to allow fixation into the patella bone stock. Other alternative fixation arrangements can be employed, for example, cast mesh, porous beads, spikes, pins or any other suitable appliance.

The posterior face 6 of the dish 2 carries a cylindrical or conical peg 7, the posterior end of which is provided with an enlarged head 8 having outwardly extending lugs 9 which project vertically upwardly and downwardly. The posterior surface is convex.

Figure 4:
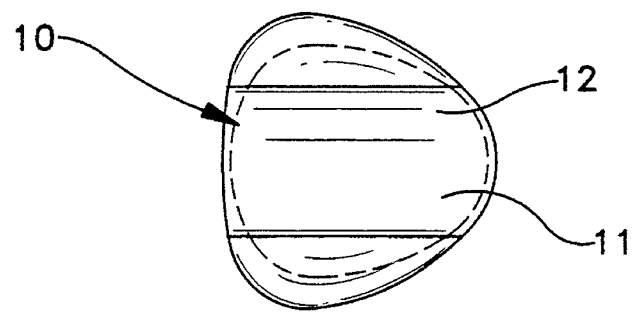
FIG. 4 is a posterior elevation of a mobile bearing component for use in the invention.
Figure 5:
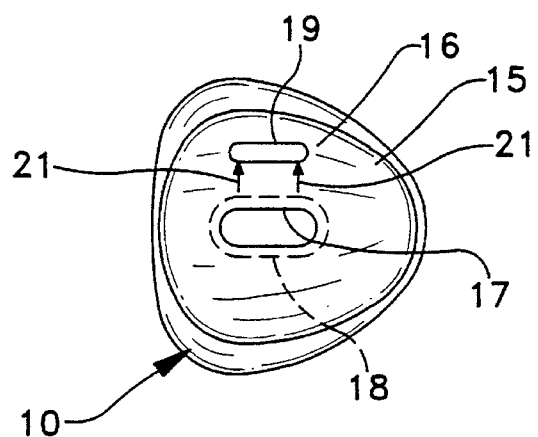
FIG. 5 is a front view of the bearing component shown in FIG. 4.
Figure 6:
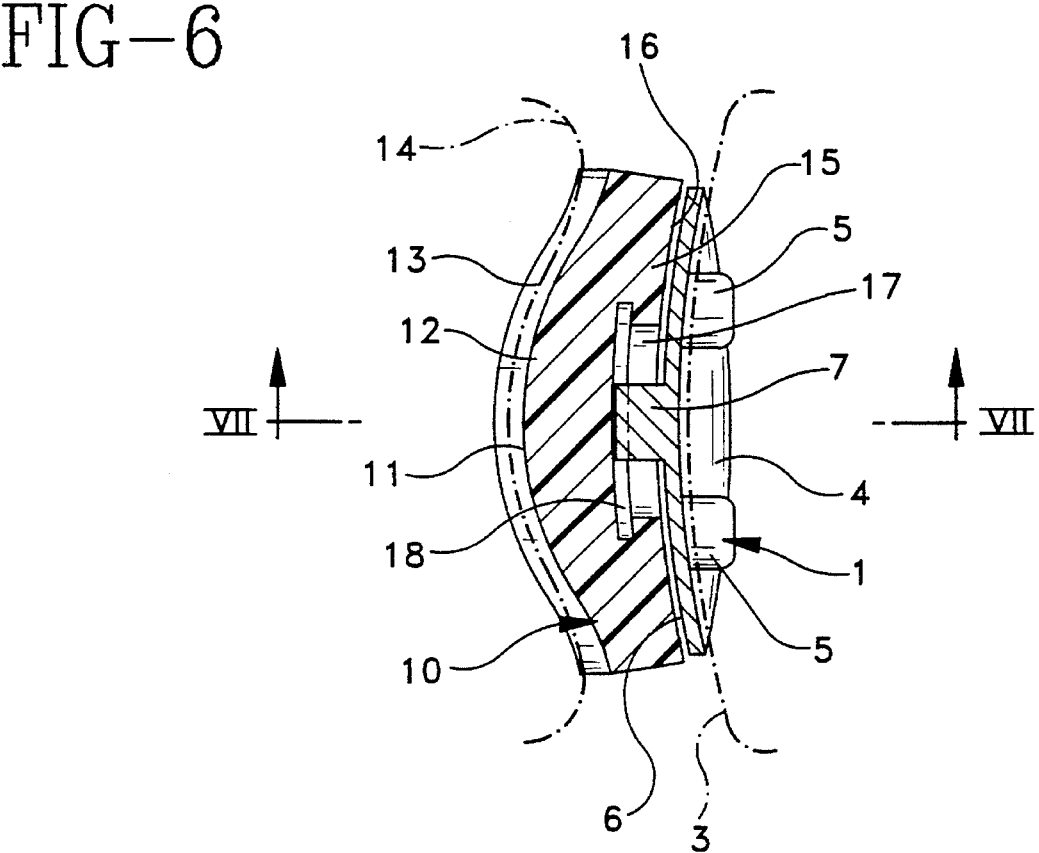
FIG. 6 is a cross-sectional plan view on the line VI—VI of FIG. 7 showing the mounting component and bearing component assembled together.
Figure 7:
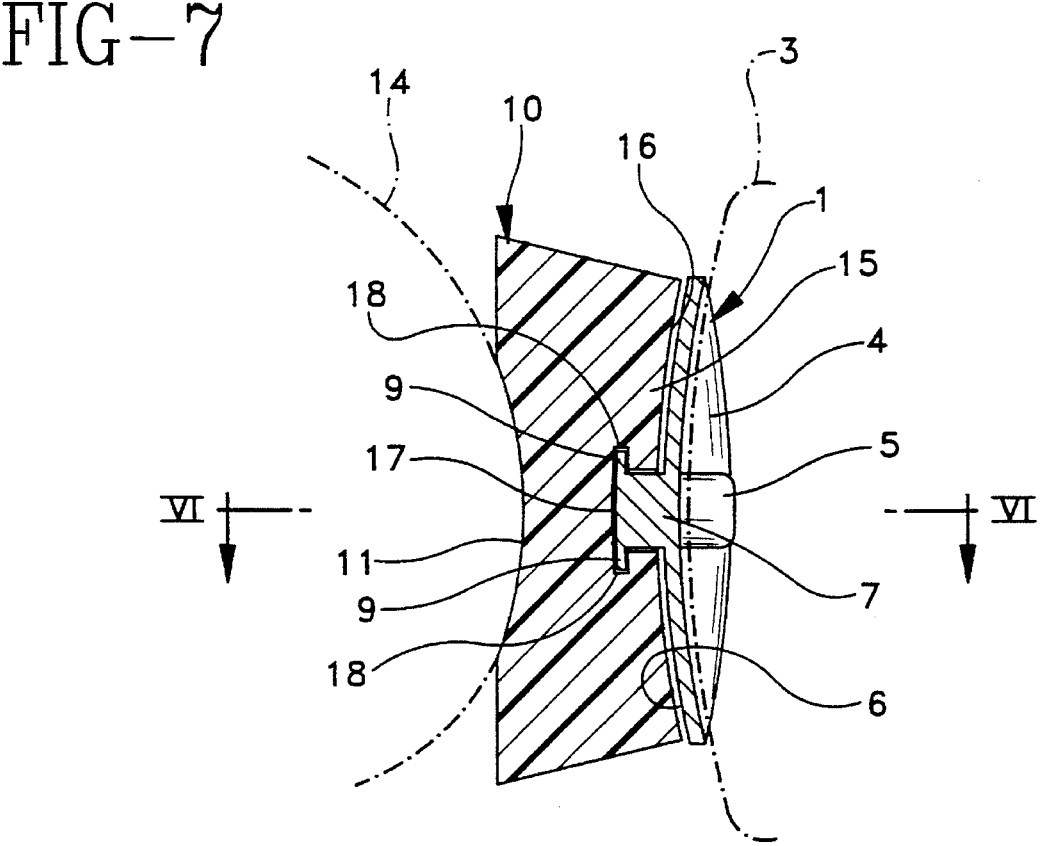
FIG. 7 is a cross-sectional side elevation taken on the line VII—VII of the assembly shown in FIG. 6.

The mounting element 1 is used with a mobile bearing component 10 as shown in FIGS. 4 and 5 and which has a first side 11 having a shaped portion 12 to engage the patella groove 13 of an artificial femoral component 14 as best shown in FIGS. 6 and 7. The second side 15 of the bearing element has a substantially spherical concave bearing surface 16 which is shaped to engage and articulate against the substantially spherical posterior convex bearing surface 6 on the mounting component 1. Located in the bearing surface 16 is a substantially horizontally extending slot 17 which is provided at its inner end with a re-entrant capture undercut 18.

A second slot 19 is also provided and which is substantially parallel with the slot 17. The dimensions of the slot 17 and the peg 7 are arranged so that the enlarged end of the peg can be inserted into the slot 17 and when rotated, the extensions 9 engage within the re-entrant undercut 18 to hold the parts together.

With the parts located together, the peg in the slot acts to restrict substantially vertical movement of the bearing component about a medio lateral axis of the knee with which it is to be used but allows substantially horizontal movement and relative rotation between the mounting component 1 and the bearing component 11. Thus it will be appreciated that the slot 17 and peg 7 together act as control means.

The bearing component 10 is constructed from resilient material, for example ultra high molecular weight polyethylene. A component is provided with two articulating surfaces, the first of which 16 articulates against the posterior surface 2 of the fixation element 1. The two surfaces are of the same geometric form so that a large contact area exists between the two components.

The geometry of the slot 17 and undercut 18 is arranged so as to allow a prescribed relative movement between the bearing component and the fixation component. This includes a nominal medio lateral shift along the length of the slot 17, and rotation of the bearing component 10 about the peg 7.

In order to accommodate surgical error and the required movement of the assembly, the limits of these movements can be set at plus or minus 3 mm of medio lateral movement. The allowable rotational movement of the bearing component 10 on the mounting element 1 may also be restricted to avoid the possibility of it dislocating inappropriately. A rotational movement of plus or minus 15° would seem to be adequate to allow this function. Limitation of this rotational movement is achieved by the provision of a pin 20 which protrudes from the convex bearing surface 6 of the mounting component 1. This pin 20 extends into the second slot 19 in the bearing surface 16 of the bearing component 10. The shape of this slot is designed to limit the rotation of the bearing component relative to the mounting component about the peg 7 in all possible medio lateral positions.

Arrows 21 on FIG. 5 show the possible range of arcuate movement which can be achieved when the peg 7 is at each end of the slot 17.

Other devices and features can be used to restrict the available rotation of bearing component 10 on the mounting element, as long as the device or feature used does not adversely affect the wear of bearing plastic material between the mounting element and the articular surface of a femoral component.

Figure 8:
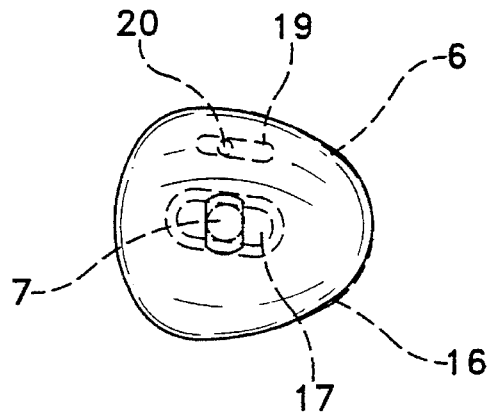
FIG. 8 is a diagrammatic posterior view of the surfaces when relative rotation has taken place.

FIG. 8 shows a typical example of the positions which the bearing surfaces 6 and 16 can achieve. In this figure the outer edge of the bearing surface 6 is shown in solid lines and the outer edge of the bearing surface 16 in broken lines.

FIGS. 6 and 7 show the assembled construction and the same reference numerals are used to indicate similar parts to those shown in the other figures.

As mentioned above, the bearing surface 11 of the bearing component 10 articulates against a prosthetic femoral component indicated by broken lines 14 in FIGS. 6 and 7. In addition, a design of this type can be used for an endo prosthetic resurfacing of a patella in which case the bearing component would be articulating against a natural femur. In the case where the bearing component is articulating against a prosthetic femur, the bearing surface 11 is arranged so that it has a high degree of conformity with the patello groove indicated at 13 on the prosthetic component 14. This is achieved by using a commonly shared male and female saddle-shaped articulating interface. This saddle-shaped interface is present on the femoral component from early flexion to deep flexion position of the articulation of the patella through the use of common transverse sectional geometry to move around a single radius of curvature in the plane of the deepest part of the patella femoral groove 13. This groove 13 in the prosthetic device may be orientated at a valgus angle equivalent to that of a normal knee, or alternatively may be neutrally included so that a single femoral component can be used in both right and left hand knees.

When the articulation is at full extension, the shape of the patello femoral groove on an actual femur or prosthetic femoral component may not be saddle-shaped due to the restrictions imposed in matching the normal anatomy and the required geometry to obtain appropriate tracking of the patella. In the embodiment of the current invention, the patello femoral grooves curvature is increased so that it tangents to the anterior cortex of the femur when the prosthetic component is put in position to accommodate the required transfer of load between the patella and the femoral component at these positions of near extension, the bearing component has two facets on its inferior and superior poles. These surfaces are arranged to be conforming with the patello femoral groove in this position of extension.

Figure 9:
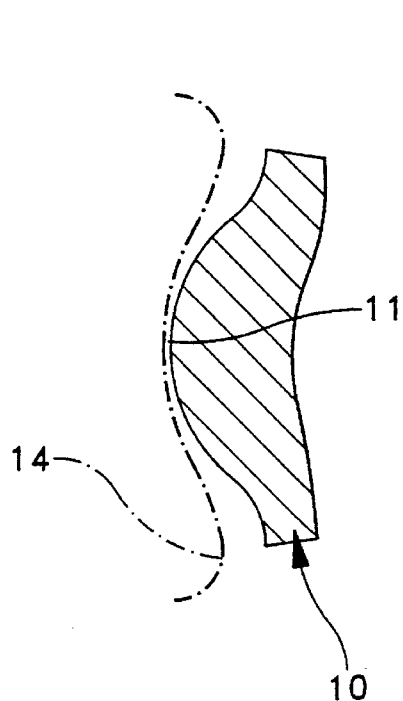
FIGS. 9 and 10 are diagrammatic cross-sectional plan views of the bearing component in position on a femoral component at different positions.
Figure 10:
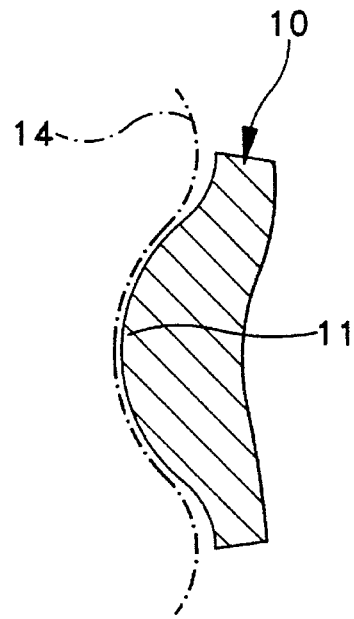

FIG. 9 shows the shape of the profile of the femoral component 14 at the position that the mobile bearing element 10 reaches when the joint is in extension and FIG. 10 shows the shape of the femoral component at the position reached by the bearing element 10 when the joint is in deep flexion.

Figure 11:
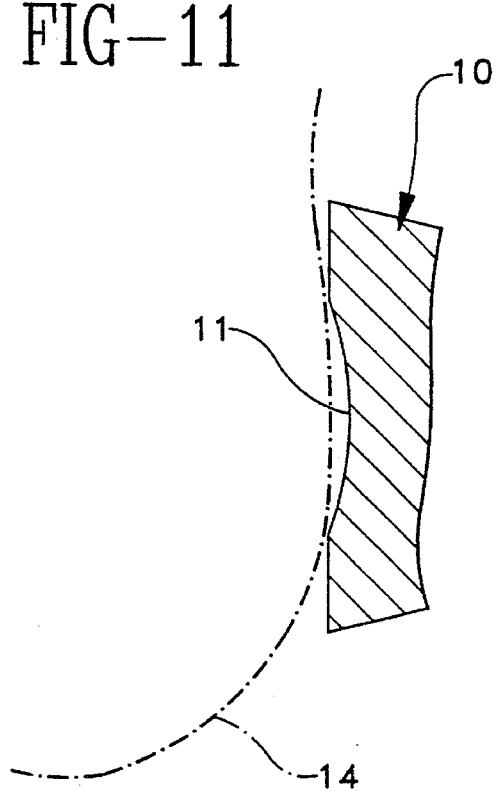
FIGS. 11 and 12 are diagrammatic cross-sectional side elevations of the bearing component on a femoral component at different positions.
Figure 12:
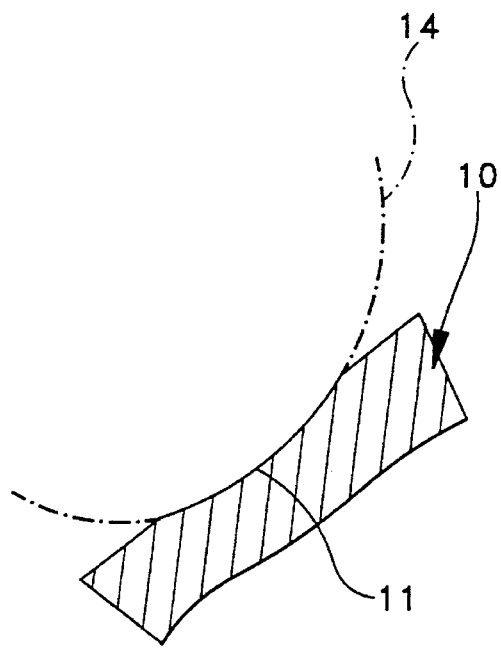

FIG. 11 shows the shape of the femoral component from one side when the joint is again in extension and FIG. 12 shows the shape and position when the joint is in deep flexion.

It will be seen that when the joint is in extension the shape of the mobile bearing element bearing surface is less conforming than it is in deep flexion. This is appropriate for the design since the higher loads are carried in deep flexion.

In designing the component as it is, it is necessary to take into account the fact that a single patella component may need to articulate with a range of sizes of the femoral component. There therefore needs to be appropriate modification of form of the articular surface on the patella to allow the maximum conformity possible with a range of alternative saddle shaped articular geometries on the femur, since these geometries cannot commonly be held across a range of sizes of the femoral components due to geometric limitations. The sectional form as shown by line 14 on FIG. 6 can be common, but the perpendicular sectional forms as in FIGS. 7, 11 and 12 vary from size to size. Nothing in this need to share and thereby comprise the conformity of the articular surfaces between the patella and the femur, however, negates the benefit of this construction.

The assembly according to the present invention incorporates two degrees of freedom of allowable movement between the bearing component and the mounting component. These accommodate the principle inaccuracies that can occur surgically in the relative positioning of the patella and femoral components.

The extensor mechanism of the knee incorporates what is known as a "Q" angle. This relates to the angle between the patello tendon and the quadriceps tendon. The orientation of the quadriceps tendon and the muscle forces exerted on it by the extensors of the knee, cause the tension in the quadriceps tendon to be directed laterally. Any design for a mobile articulation of this type must therefore accommodate this lateralizing force.

The tendinous structures on the patella can exert various force on the fixation element of this construction. It can be shown that in order to obtain a stable equilibrium situation, the spherical surface 6 on the mounting component must allow the resultant vector from the tendinous and ligament forces exerted on the patella to be balanced by the contact force from the articulation of the component against the femur. Due to the low friction at the interface between the bearing component and the mounting component, the contact force must cross this boundary perpendicularly. It can therefore simply be shown that a convex bearing surface on the mounting component is required.

I claim:

1. A prosthetic patello femoral joint assembly comprising a patella femoral joint having a patella mounting component including a movable mobile bearing component, a first side of which is shaped to engaged the patella groove of a natural or an artificial femoral component, and a second side of which has a substantially spherical concave bearing surface which engages and can articulate against a substantially spherical posterior convex bearing surface on said mounting component, and a control element acting between the components which restricts substantially vertical movement of the bearing component relative to the mounting component about a medio-lateral axis of the knee with which it is to be used, but allow substantially medio-lateral movement and relative rotation between said mounting component and said bearing component wherein said control element comprises a peg carried on said mounting component which engages a substantially horizontal slot in said bearing component, said peg comprising a post part with a flange at its posterior end which is held in an undercut in said horizontal slot, and wherein a second control element acts to limit relative rotational movement between said mounting component and said bearing component.

2. A prosthetic patello femoral joint assembly as claimed in claim 1 in which said second control element comprises a pin which engages a second slot in said bearing component.

3. A prosthetic patello femoral joint assembly as claimed in claim 2 in which said pin is smaller than said second slot to provide a clearance in second slot.

4. A prosthetic patello femoral joint assembly as claimed in claim 3 in which said second slot is substantially parallel with said first slot and said pin includes a clearance in said second slot to allow limited rotation of said bearing component about said peg, said rotation being accommodated within said clearance of the pin in said second slot.

5. A prosthetic patello femoral joint assembly as claimed in claim 1 including a prosthetic femur component adapted for connection to a suitably prepared femur and having a patella groove to receive said bearing component.

* * * * *